United States Patent [19]
Krause et al.

[11] Patent Number: 5,925,346
[45] Date of Patent: Jul. 20, 1999

[54] ANTISENSE STRATEGY FOR THE PRODUCTION OF SPECIES SPECIFIC VIRAL INSECTICIDES

[75] Inventors: Margarida Krause, Fredericton, Canada; Xinyong Qu; Wenbin Chen, both of Brisbane, Australia

[73] Assignee: Queen's University at Kingston, Kingston, Canada

[21] Appl. No.: 08/457,752

[22] Filed: Jun. 1, 1995

[51] Int. Cl.$^6$ .............................. A01N 63/00; C12N 7/01; C12N 15/79; C12N 15/86
[52] U.S. Cl. .................. 424/93.2; 435/172.3; 435/320.1; 514/44; 536/23.1; 536/24.5
[58] Field of Search .......................... 514/44; 435/320.1, 435/172.3; 536/23.1, 24.5; 424/93.2

[56] References Cited

U.S. PATENT DOCUMENTS

| | | | |
|---|---|---|---|
| 4,870,023 | 9/1989 | Fraser et al. | 435/235.1 |
| 5,004,687 | 4/1991 | Miller | 435/69.1 |
| 5,071,748 | 12/1991 | Miller | 435/69.1 |
| 5,155,037 | 10/1992 | Summers | 435/348 |
| 5,162,222 | 11/1992 | Guarino et al. | 435/348 |
| 5,169,784 | 12/1992 | Summers et al. | 435/320.1 |
| 5,180,581 | 1/1993 | Miller et al. | 424/93.2 |
| 5,266,317 | 11/1993 | Tomalski et al. | 424/93.2 |
| 5,278,050 | 1/1994 | Summers | 435/69.1 |
| 5,298,418 | 3/1994 | Granados | 435/348 |
| 5,300,435 | 4/1994 | Granados | 435/348 |

OTHER PUBLICATIONS

Sivasubramanian et al., "Development of novel genetically engineered antisense insect viruses as improved viral insecticides", *J. Cell. Biochem.*, Suppl. 15D: 33, 1991.

Bradley, M.O., et al. Reversal of transformed phenotypes by antisense fos. *Annals of the New York Academy of Sciences* 660: 124–135 (Oct. 1992).

Caskey, C.T. Anstisense and differentiation. *Annals of the New York Academy of Sciences* 660: 154–158 (Oct. 1992).

Gewitz, A.M. Therapeutic applications of antisense DNA in the treatment of human leukemia. *Annals of the New York Academy of Sciences* 660: 178–187 (Oct. 1992).

Green, D.R., et al. Antisense oligodeoxynucleotides as probes of T–lymphocyte gene function. *Annals of the New York Academy of Sciences* 660: 193–203 (Oct. 1992).

Jacobs–Lorena, M. Interference of gene expression in Drosophila by antisense ribosomal protein genes integrated into the germ line. *Annals of the New York Academy of Sciences* 660: 204–208 (Oct. 1992).

McGaughey, W.H. Problems of insect resistance to *Bacillus thuringiensis* (corrected version of NT932). *Agriculture Ecosystems & Environment* 49: 95–102 (1994).

Stewart, L. et al. Construction of an improved baculovirus insecticide containing an insect–specific toxin gene. *Nature* 352: 85–88 (Jul. 1991).

Tomalski, M.D. & Miller, K. Insect paralysis by baculovirus–mediated expression of a mite neurotoxin gene. *Nature* 352: 82–85 (Jul. 1991).

Van Eldik, L.J., et al. Antisense approaches to the function of glial cell proteins. *Annals of the New York Academy of Sciences* 660: 219–230 (Oct. 1992).

Walker, C.W. et al. First non–vertebrate member of the myc gene family is seasonally expressed in an invertebrate testis. *Oncogene* 7: 2007–2012 (1992).

Zatloukal, K., et al. Transferrinfection: A highly efficient way to express gene constructs in eukaryotic cells. *Annals of the New York Academy of Sciences* 660: 136–153 (Oct. 1992).

*Primary Examiner*—Jasemine C. Chambers
*Assistant Examiner*—Scott D. Priebe
*Attorney, Agent, or Firm*—John R. Rudolph; Carol Miernicki Steeg

[57] ABSTRACT

A novel type of insect control agent and methods for controlling insect pests are described. The agent consists of a vector, such as a baculovirus of the polyhedral inclusion body type, containing in an antisense orientation cDNA sequence which has been derived from the complete sense sequence of a gene which is essential for the growth and development of the host from which the sequence is derived. In order for the insect control agent to exert its effect the insect pests which are to be controlled must be susceptible to the vector. Specifically described are the sequences from *Choristoneura fumiferana* and the human c-myc gene as well the methods of production and use of these agents.

**24

Nucleotide Sequence of cloned C. fumiferana c-myc-Related exon 2

```
                                                              50
CCAGTGAGGA  CATTTGGAAG  AAGGTATAAT  TTAGGTGCGT  TAAGTAGCAG
                                    BOX A
                                                             100
AAACATCAAT  TCCTTATTTT  AATTTCCAAG  AAAATGGTAA  TTATACAGGT
                                                             150
GATTCGGGAG  TGAGCAGGAC  CAACCAGCAG  TATTTAGTAA  GTTCTTTTTG
                                                             200
TTTTAATGTT  CGCATACAGA  ATTAAAGTAC  CATAATTAAA  GTGTGGGTGG
                                                             250
GGTTTACTAA  ATATGATTGT  GAAGGACCCA  TTATGAATTA  CTGAGGGTGT
                                                             300
AATTGTTCCT  GCTTACGTCT  CCTGAATTAC  ACTATAGTAC  CGACGTTAGG
BOX B
                                                             350
CATTTCAGGA  AAACTCACTG  TTTTCCTGCA  GTTTGTACAA  GAAGAAATCC
                   370
CTCTGCTGTA  TGCCCATACC
BOX C
```

Human c-myc Exon 2 Fragment
(sequence 4651-5407)

```
                                                              4700
CGCCCAGCGA   GGATATCTGG   AAGAAATTCG   AGCTGCTGCC   CACCCCGCCC

4750
CTGTCCCCTA   GCCGCCGCTC   CGGGCTCTGC   TCGCCCTCCT   ACGTTGCGGT

4800
CACACCCTTC   TCCCTTCGGG   GAGACAACGA   CGGCGGTGGC   GGGAGCTTCT

4850
CCACGGCCGA   CCAGCTGGAG   ATGGTGACCG   AGCTGCTGGG   AGGAGACATG

4900
GTGAACCAGA   GTTTCATCTG   CGACCCGGAC   GACGAGACCT   TCATCAAAAA

4950
CATCATCATC   CAGGACTGTA   TGTGGAGCGG   CTTCTCGGCC   GCCGCCAAGC

5000
TCGTCTCAGA   GAAGCTGGCC   TCCTACCAGG   CTGCGCGCAA   AGACAGCGGC

5100
CCTGCAGGAT   CTGAGCGCCG   CCGCCTCAGA   GTGCATCGAC   CCCTCGGTGG

5050
AGCCCGAACC   CCGCCCGCGG   CCACAGCGTC   TGCTCCACCT   CCAGCTTGTA

5150
TCTTCCCCTA   CCCTCTCAAC   GACAGCAGCT   CGCCCAAGTC   CTGCGCCTCG

5200
CAAGACTCCA   GCGCCTTCTC   TCCGTCCTCG   GATTCTCTGC   TCTCCTCGAC

5250
GGAGTCCTCC   CCGCAGGGCA   GCCCCGAGCC   CCTGGTGCTC   CATGAGGAGA

5300
CACCGCCCAC   CACCAGCAGC   GACTCTGGTA   AGCGAAGCCC   GCCCAGGCCT

5350
GTCAAAAGTG   GGCGGCTGGA   TACCTTTCCC   ATTTTCATTG   GCAGCTTATT

5400
TAACGGGCCA   CTCTTATTAG   GAAGGAGAGA   TAGCAGATCT   GGAGAGATTT

5407
GGGAGCT
```

FIGURE 4

ANTISENSE STRATEGY FOR THE PRODUCTION OF SPECIES SPECIFIC VIRAL INSECTICIDES

TECHNICAL FIELD

The present invention relates to methods and compositions for improved biological control of insect pests. More particularly, the present invention relates to molecular engineering of baculoviruses and the production of recombinant viruses containing antisense constructs of a gene essential to the growth and development of the target insect pest.

BACKGROUND OF THE INVENTION

Conventional chemical pesticides used to control insect pest populations in target crops generally affect beneficial as well as non-beneficial species. Unfortunately through repeated treatments target insect pests have been found to acquire resistance to such chemicals allowing new pest populations to rapidly develop which are resistant to these pesticides. Consequently, new, and potentially more toxic, chemicals must be developed. Furthermore, chemical pesticides pose potential environmental hazards and health concerns, and it is the combination of such factors which has generated considerable concern about the widespread use of broad-spectrum chemical insecticides. This concern has led to research into alternative methods of controlling insect pests.

Biological control represents an important alternative to traditional chemical insect pest control strategies. The two primary approaches of biological control include deployment of naturally occurring organisms which are pathogenic, and, the development of insect resistant crops. With respect to the use of naturally occurring organisms, insect pathogens such as baculoviruses have attracted particular attention because many naturally occurring baculoviruses presently infect insects which are pests of commercially important agricultural and forestry crops. Furthermore, (1) one baculoviruses as a group found solely in arthropods, and (2) individual baculovirus strains are usually restricted in their replication to one or a few species of insects. Consequently, they can be targeted to those species which are sought to be controlled. As such they pose little risk, if any, to man or the environment and can be used without detriment to beneficial insect species. Baculoviruses are therefore potentially valuable as biological control agents.

Baculoviruses are typically packaged in two forms: nucleocapsids may be occluded in the nucleus of infected cells in particles known as "polyhedral inclusion bodies" (PIBs) of which the predominant structural protein is polyhedrin, or, they may bud through the membrane of the infected cell, thereby acquiring a membrane envelope to form non-occluded virus (NOV) particles. Baculovirus subgroups include nuclear polyhedrosis viruses (NPV), granulosis viruses (GV) and non-occluded baculoviruses. In occluded forms of baculoviruses (NPV and GV sub-groups), the virions' enveloped nucleocapsids are embedded in a crystalline protein matrix. This structure, referred to as an inclusion or occlusion body is the form found extraorganismally in nature and is responsible for spreading the infection between organisms. A characteristic feature of viruses of the sub-group NPV is that many virions are embedded in each occlusion body. The crystalline protein matrix of the occlusion bodies is primarily composed of a single polypeptide which is known as polyhedrin or granulin.

The polyhedrin protein is the product of a viral gene which is expressed very late in the viral reproductive cycle, i.e., well after completion of viral DNA replication. This gene is under the control of a powerful promoter and consequently large quantities of the polyhedrin protein are produced during late infection stages to produce PIBS. Upon cell lysis and insect death PIBs are released into the environment and can last for extended periods until ingested by other insects which will start a new round of viral replication. Non-occluded virus are only viable within the original insect host.

One of the major drawbacks to the use of baculoviruses as a means to achieve insect pest control is the length of time which elapses between the time the baculovirus is ingested by the insect and the time the insect finally dies. Insect larvae infected with such viruses continue feeding for several days after infection and die only when maximum crop damage has occurred.

There have been a number of attempts to provide viruses with the capacity to generate more rapid lethality in the host by introducing genes for neuropeptides or neurotoxins into viral DNA. However, to date, this approach has not provided a solution to the problem, possibly due to difficulty in the expression and processing of products coded by these genes. On the other hand, some success has been generated through introduction into the viral genome of toxin-producing genes from other arthropods, eg., a mite which produces a paralysing toxin when feeding on its host (Tomalski, M. D. & Miller, K., Nature 352, 82–85, 1991; Tomalski and Miller, U.S. Pat. No. 5,266,317; Stewart, L. et al. Nature 352, 85–88, 1991). Unfortunately however, as with the traditional approach using chemical insecticides, there is the possibility of host resistance being developed to the toxin introduced by this methodology. For example, in the case of *B. thuringiensis* toxin there has been the development of a resistance in the range of target insect pests (see McGaughey, W. H., Agriculture Ecosystems & Environment, 49: 95–102, 1994).

The present invention provides a unique strategy to achieve insect pest control, involving the elimination of the function of a gene essential for insect development in the target insect pest, the effect of which is to almost immediately cease insect growth and development. This is accomplished by introducing a portion of a selected gene, downstream from a powerful viral promoter in an orientation such that when the gene portion is transcribed, an antisense RNA transcript is produced. The complete gene is not required and may not even be fully characterized; a small portion of the antisense transcript is sufficient to completely block translation of the corresponding cellular gene from the host insect. The selected gene is one which encodes a protein which is essential for the growth and development of an insect or other organism from which the gene is obtained.

Antisense strategies have previously been utilized to inhibit expression of a variety of genes responsible for specific human and animal disease. A compilation of these has appeared in a recent issue of The Annals of New York Academy of Sciences (Volume 660, Oct. 28, 1992). Most of these strategies involved the use of antisense oligonucleotides targeted to the translation start site of the messenger RNA so as to inhibit ribosomal binding at the start of protein translation, thus cancelling out expression from the gene. Although such strategies have worked, they rely on vast quantities of oligonucleotides to overcome the low efficiency of their entry into living cells, and the effect is soon lost as the oligonucleotides are degraded. In contrast the approach described here involves the use of a carrier virus which not only has privileged access into insect tissues, but is also capable of propagating itself within the host, thus maximizing the effect of the antisense sequences transcribed from its genome.

In the present invention the selected inserted sequence is a gene fragment downstream from the translation start site comprising three conserved stretches of nucleotides, which is inserted into the start of the polyhedrin gene in an orientation such that when transcribed, an antisense RNA transcript is produced. It has been confirmed that abundant transcripts containing the inserted sequence are produced from the polyhedrin promoter and that translation of the polyhedrin protein is blocked as a consequence of the insertion. It is believed that these antisense transcripts block translation of a corresponding native mRNA to produce a protein.

It should be understood that any portion of any gene which will interfere with the production of any cell product which is required for development in the organism should be sufficient for the purposes of this invention. It should also be understood that the gene, or gene portion, can be inserted anywhere downstream from a strong viral promoter so long as it is inserted in an orientation wherein an antisense transcript is produced and in a position to result in the effect of stopping insect growth and development.

The present invention includes all target insect pests which are susceptible to infection by baculoviruses as well as any other insect and vector combination wherein the vector is capable of stopping insect growth and development through implementation of the antisense strategy employed herein. It also includes all genes in a given target insect pest which are required for insect development in the target insect pest.

The present specification includes a method for construction and testing of recombinant baculovirus which produces antisense transcript corresponding to any gene which is required for insect development in the target organism, in an amount sufficient to completely block expression of the corresponding cellular gene from the host insect.

SUMMARY OF INVENTION

The present invention provides an insect control agent which is a vector comprising a DNA sequence derived from a gene which is essential for growth and development of the host of the gene, wherein the DNA sequence is oriented such that when it is transcribed, an antisense RNA transcript, relative to the sense direction of c-myc, is produced, and wherein the insect is one of any insect species susceptible to said vector.

In a preferred embodiment, the vector just mentioned is a baculovirus of the polyhedral inclusion body type. Other baculovirus types such as granulosis virus can also be used.

In a further embodiment the host is human and the DNA sequence comprises sequences of the human c-myc gene.

In a yet further embodiment of the invention, the host is *C. fumiferana* and the DNA sequence is a PCR product prepared using conserved sequences of the human c-myc gene as PCR primers.

In another embodiment the host is *C. fumiferana, the DNA and the sense sequence is as in SEQ ID NO 1*, and the DNA sequence is inserted downstream from the polyhedrin promoter in an orientation such that when it is transcribed, an antisense RNA transcript is produced.

In another embodiment the sequence of a portion of the human c-myc gene as in SEQ ID NO 2 is inserted downstream from the polyhedrin promoter in an orientation such that when it is transcribed, an antisense RNA transcript is produced.

In yet a further embodiment, the baculovirus comprises the DNA sequence of SEQ ID NO 1 inserted downstream of the polyhedrin promoter at the position of the multiple cloning site designated in the BLUEBAC vector plasmid (a baculovirus vector from Invitrogen) in an orientation such that when it is transcribed, an antisense RNA transcript is produced.

In yet another embodiment, the insect control agent is a baculovirus comprising the DNA sequence of SEQ ID NO 2 inserted downstream of the polyhedrin promoter at the position of the multiple cloning site designated in the BLUEBAC vector plasmid in an orientation such that when it is transcribed, an antisense RNA transcript is produced.

The present invention also provides a method of controlling insect pests by infecting the insects with a vector comprising a DNA sequence is derived from a gene which is essential for growth and development of the host of the gene, wherein the DNA sequence is oriented such that when it is transcribed, an antisense RNA transcript is produced. The insects which will be controlled are of any insect species susceptible to the vector.

In a preferred embodiment of this method, the vector is a baculovirus of the polyhedral inclusion body type. Other baculovirus types such as granulosis virus can also be used.

In a further preferred embodiment of this method, the host is human and the DNA sequence comprises conserved sequences of the human c-myc gene.

In another embodiment of the method, the host is *Choristoneura fumiferana* and the DNA sequence is a PCR product prepared using conserved sequences of the human c-myc gene as PCR primers.

In yet further embodiments of the method the host is *Choristoneura fumiferana* and the DNA sequence is as in SEQ ID NO 1, or the host is human and the DNA sequence is as in SEQ ID NO 2.

In a further embodiment of the method, the DNA sequence chosen is inserted downstream of the polyhedrin promoter in the baculovirus vector at the position of the multiple cloning site designated in the BLUEBAC plasmid in an orientation such that when it is transcribed, an antisense RNA transcript is produced.

In a further embodiment, the method of controlling insects is by infecting the insects with an insect control agent wherein the insect control agent is a baculovirus comprising the sequence of SEQ ID NO: 1 inserted downstream of the polyhedrin promoter at the position of the multiple cloning site designated in the BLUEBAC vector plasmid in an orientation such that when it is transcribed, an antisense RNA transcript is produced.

In yet a further embodiment of the method of controlling insects, the insects are infected with an insect control agent wherein the insect control agent is a baculovirus comprising the sequence of SEQ ID NO: 2 inserted downstream of the polyhedrin promoter at the position of the multiple cloning site designated in the BLUEBAC vector plasmid in an orientation such that when it is transcribed, an antisense RNA transcript is produced.

DEFINITIONS

The following terms and abbreviations have the meanings indicated:

As used in this specification, "PCR" means polymerase chain reaction.

As used herein "SDS-PAGE" means sodium dodecyl sulphate polyacrylamide gel electrophoresis.

As used herein "PFU" means plaque-forming units and "Sf9" cultured cells means a cell line obtained from *Spodoptera frugiperda*.

As used herein "instar" means a larval stage and "AcM-NPV" means *Autographa californica nuclear polyhedrosis virus.*

As used herein "Grace's insect growth medium" is a common formulation used to culture insect cells.

Also, as used herein, "Sbw" means eastern spruce budworm, which is *Choristoneura fumiferana* (or *C. fumiferana*).

BRIEF DESCRIPTION OF THE DRAWINGS

FIG. 1 illustrates the nucleotide sequence of cloned *C. fumiferana* DNA related to c-myc exon 2(SEQ ID NO: 1).

FIG. 4 illustrates the nucleotide sequence of Human c-myc exon 2 fragment between positions 4651 and 5407 inclusive (SEQ ID NO: 2).

DETAILED DESCRIPTION OF THE INVENTION.

Construction of Recombinant Virus

A number of degenerate and non-degenerate oligo-nucleotides have been designed which correspond to the conserved sequences of the c-myc gene, one for each of the transcription activation domains (boxes A, B and C) and for the two helical sequences of the DNA-binding domain (helix-loop-helix-zipper domain) of the c-myc protein. These oligo-nucleotides were used in various combinations as forward and reverse primers for PCR amplification of genomic DNA from *C. fumiferana*. The products were screened by Southern hybridization with a vertebrate c-myc probe at low stringency and the selected fragments were cloned and sequenced. The gene product of the c-myc gene, the c-myc protein, is known to be essential in all tissues undergoing cell division, cell differentiation and pro-grammed cell death. The c-myc protein is a transcription activator of other genes involved in the control of the cell division cycle. Functional domains of this protein have been found to be well conserved in their amino acid sequences between different classes of vertebrates and one invertebrate organism (Walker, C. W., et al *Oncogene* 7: 2007–2012, 1992). Although the c-myc gene has not yet been found in insects, the known conserved sequences of the c-myc gene have been used here to design oligo-nucleotide primers for amplification by PCR of DNA sequences encoding putative equivalent proteins in several insects.

The sequence of the clone obtained by PCR amplification of *C. fumiferana* DNA and selected for viral construction is identified as SEQ ID NO: 1. Shows SEQ ID NO: 1 with the transcription activation domains identified and underlined as Boxes A, B and C.

The selected *C. fumiferana* clone was obtained with primers designed for boxes A and C; thus homology of these portion of the clone with the corresponding vertebrate sequences was high (80 and 60% respectively). However homology with box B was only 45%, possibly indicating wide divergence between insect and vertebrate c-myc or related genes.

Figure 2A:
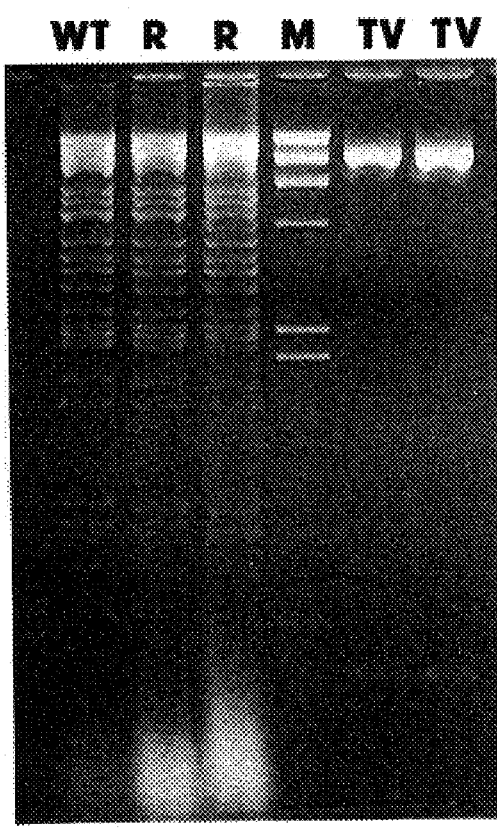
FIG. 2A–B shows Southern blot hybridizations using the cloned sequence from *C. fumiferana* which corresponds to the conserved sequences of the c-myc gene, as a probe confirming the presence of the inserted *C. fumiferana* sequence in the baculovirus recombinant and transfer vector (BLUEBAC plasmid from Invitrogen).
Figure 2B:
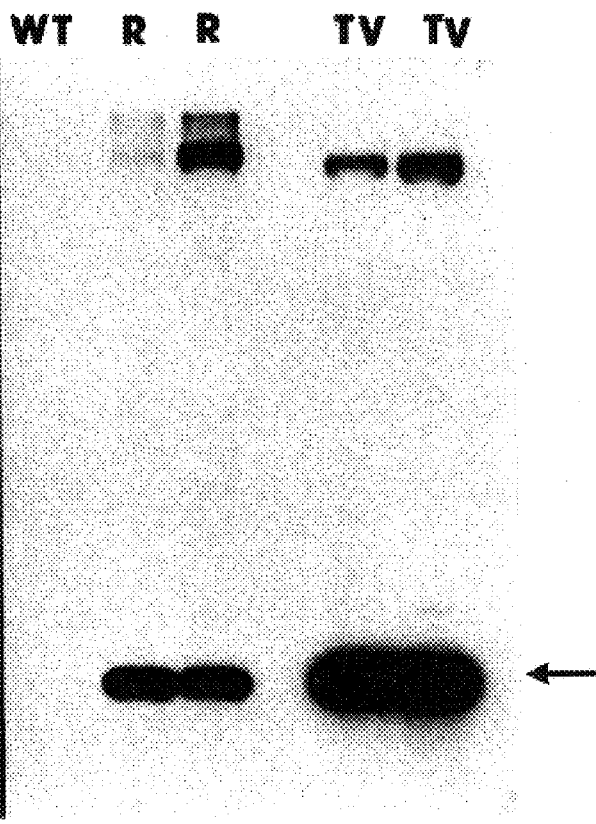

This particular sequence was inserted into a selectable, polyhedrin promoter based baculovirus transfer vector (BLUEBAC plasmid from Invitrogen) downstream from the polyhedrin promoter in an orientation such that upon transcription, an antisense RNA would be produced. The resulting plasmid was isolated and cotransfected with DNA from wild type baculovirus, AcMNPV, into Sf9 cultured cells. Recombinant viral plaques were selected for the presence of a marker gene of the vector (β-galactosidase, which produces a blue colour with the appropriate substrate) and the absence of polyhedrin inclusion bodies (PIBs) due to removal of the polyhedrin gene. Pure recombinant preparations were obtained by several cycles of infection of selected blue plaques into cultured cells. Confirmation of the presence of the inserted *C. fumiferana* sequence was obtained in Southern blot hybridizations using the cloned sequence as a probe. FIG. 2 illustrates the results from the Southern blot where A is an ethidium bromide-stained gel, and B is the Southern hybridization of the ethidium bromide-stained gel with the cloned *C. fumiferana* sequence. W represents DNA from wild type virus, while R represents DNA from the recombinant virus, M represents a molecular weight marker (kiloDaltons), and TV represents a transfer vector. The arrow points to the position of the cleaved insert on virus and vector.

Figure 3A:
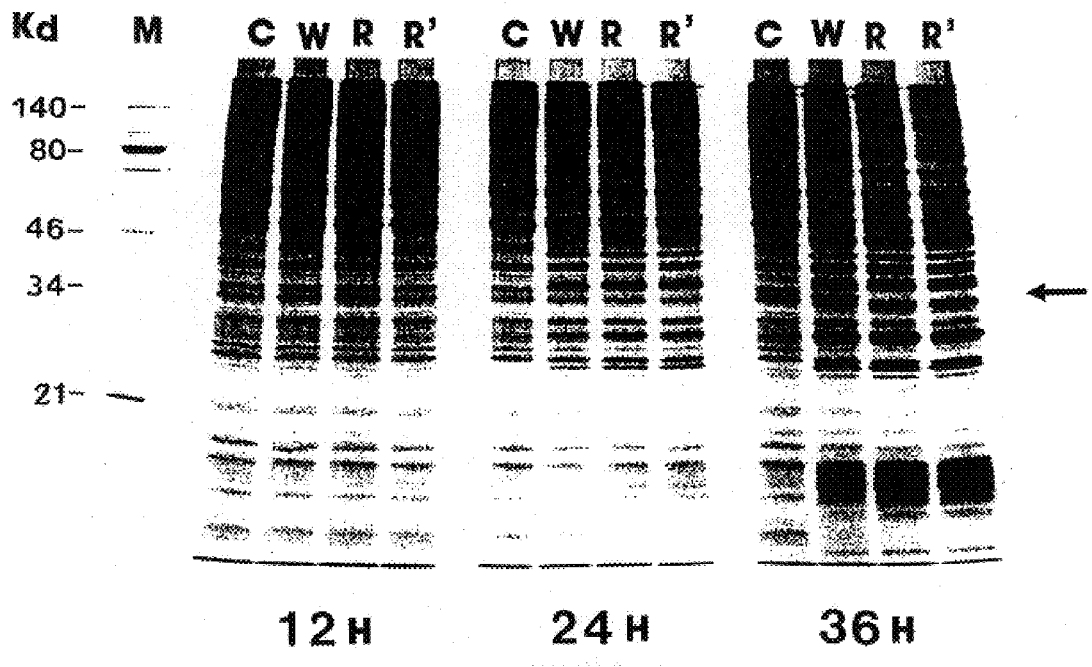
FIG. 3 shows an autoradiograph of $^{35}$S-labelled proteins extracted from uninfected Sf9 cells (C) and wild type/(W) or recombinant virus-infected (R, R$^1$) Sf9 cells, and represents a comparison of the respective polypeptide patterns obtained by SDS-PAGE separation of the protein extracts which were obtained at various times post infection.
Figure 3B:
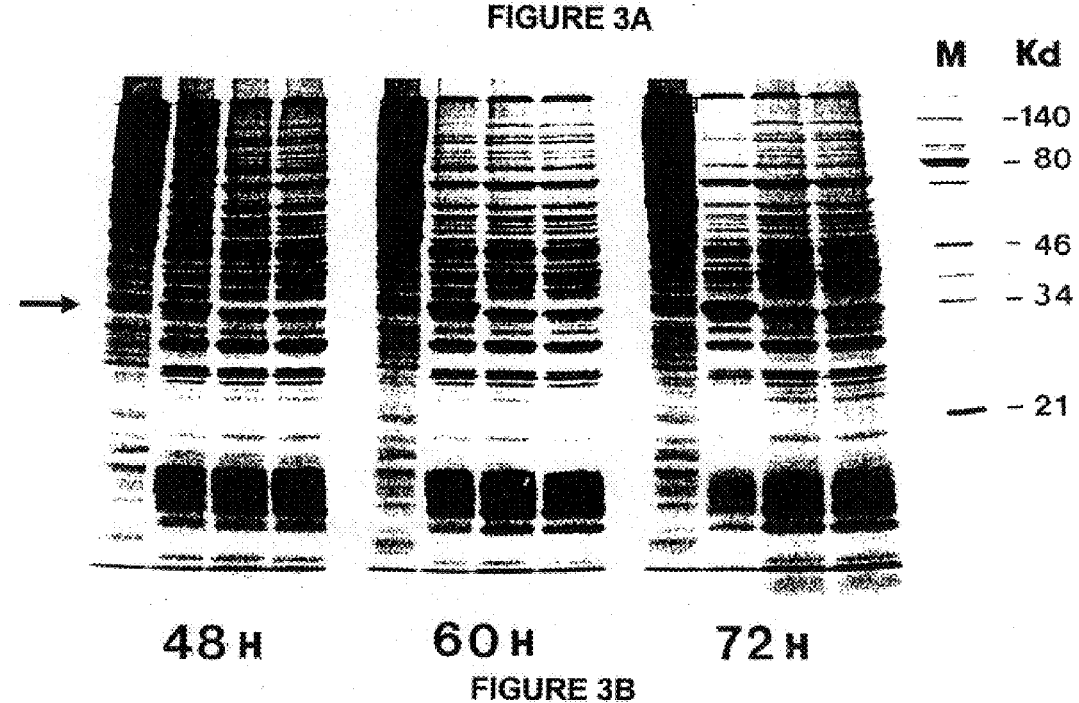

Protein extracts of uninfected, wild type virus-infected and recombinant virus-infected Sf9 cells were then compared on the basis of polypeptide patterns obtained by SDS-PAGE separation. FIG. 3 illustrates the results of this separation procedure wherein M refers to a molecular weight marker (kiloDaltons), and the arrows point to the position of the polyhedrin protein seen on W lanes. The appearance of the polyhedrin protein can be detected at 36 hours post-infection only in cells infected with wild type virus (lanes W).

BIOASSAYS IN *S. FRUGIPERDA* LARVAE

Figure 5:
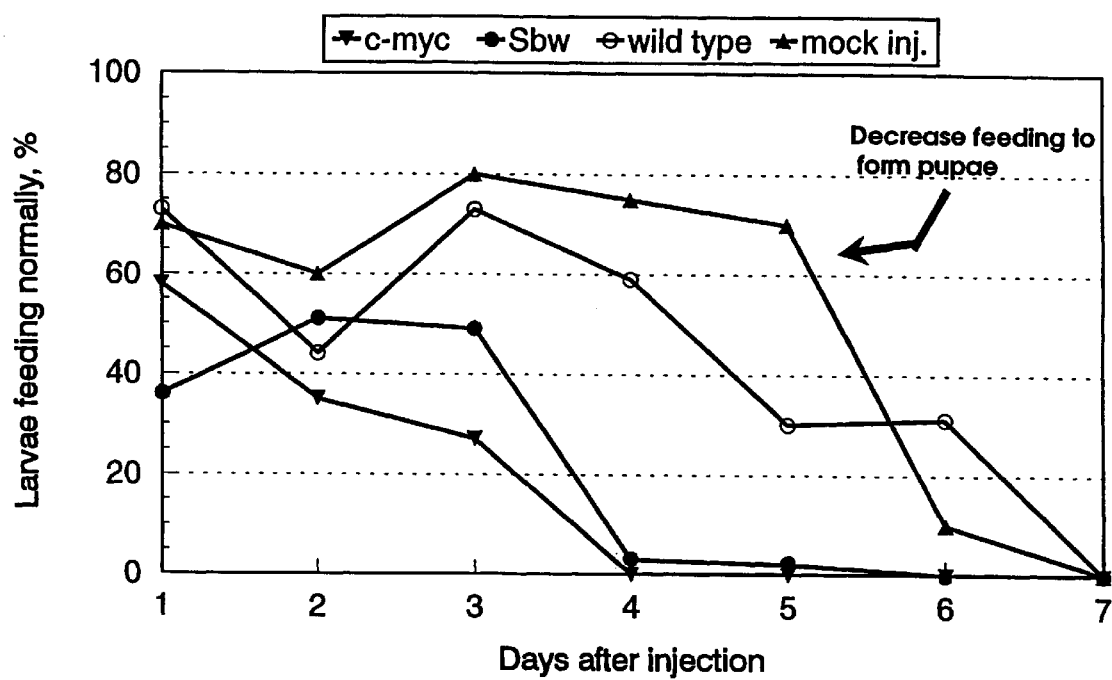
FIG. 5 provides a graphic representation of the effects of antisense recombinants viruses containing the human c-myc and *C. fumiferana* inserts in comparison with the wild type virus, on larval feeding as a function of time after infection.
Figure 6:
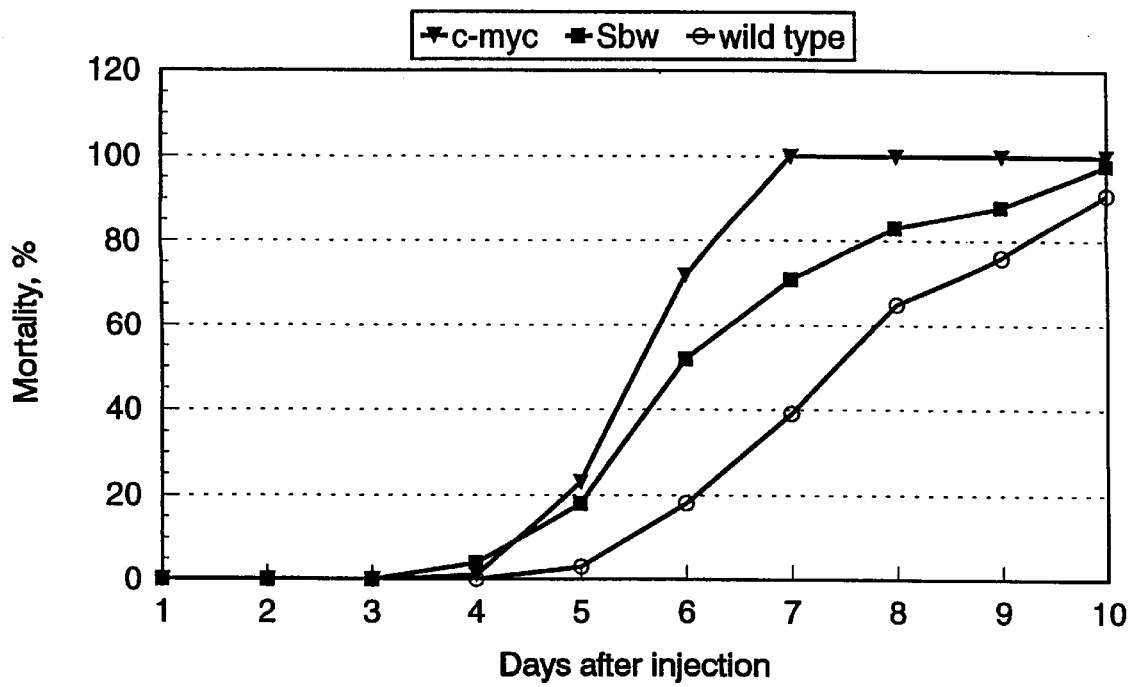
FIG. 6 provides a graphic representation of the effects of antisense recombinant viruses containing the human c-myc and *C. fumiferana* inserts in comparison with the wild type virus, on larval mortality as a function of time after infection.

The following details of treatments and viral dosages pertain to FIG. 5 and FIG. 6. Four groups of 4th instar *S. frugiperda* larvae were used for bioassays with approximately 100 larvae (average body weight of 126 mg) in each group. Each group was infected with 2 μl of either Grace's insect growth media ("mock injection") or 2 μl of 2×10$^7$ PFU/ml wild type virus or one of two recombinant viruses. The two recombinants tested contained inserts of either human c-myc exon 2 which is presented as SEQ. ID NO: 2(the 757 nucleotides are from position 4650 to 5407 of the HUMMYCC Genbank data base sequence, the positions of which are presented in FIG. 4), or the corresponding PCR product from *C. fumiferana* (SEQ. ID NO: 1) in antisense orientation. In each case, the insert was oriented such that upon transcription, an antisense c-myc-related transcript is produced. The use of the previously known human c-myc sequence was designed to test the possibility that conserved sequences of this gene family would be found in insects, other than the product obtained from *C. fumiferana* which has yet to be characterized as belonging to the c-myc family genes. The groups were observed post-injection and cessation of feeding as well as time of death were recorded in each case. All larvae injected with Grace's medium developed normally. As indicated by the arrow, decreased feeding in that group was due to normal pupa development between 5 and 7 days after treatment. Oscillation in feeding within days 1 and 2 are also due to variable amounts of molting since larvae stop feeding during normal molting from which they normally recover.

As can be seen from the data presented in FIG. 5 both antisense recombinants have a marked effect on feeding, which is almost completely stopped after day 4. Also, note that the effect of the antisense transcripts is evident starting at day 3, the time of maximal expression of the polyhedrin gene (compare the results in FIGS. 5 and 6 with FIG. 3, lane W).

In contrast, wildtype virus-injected larvae go on feeding for 3 more days. None of the recombinant virus-injected larvae developed into pupae, while only 1% of the wildtype—and 100% of the mock-injected larvae pupated normally. The mechanism of these effects is still under investigation, however, regardless of the mechanism it is clear that both antisense recombinants are effective in stopping larval feeding, the c-myc gene fragment appearing to be more effective than the Sbw PCR product.

Data from an analysis for larval mortality as a function of time post-injection is presented in FIG. 6. The data presented illustrate marked differences between wildtype virus- and recombinant virus-injected larval groups, with the recombinants, and in particular the c-myc recombinant, demonstrating a rate which is 3 days faster than that caused by the human wildtype virus.

In these experiments the larvae were infected by injection, however they can also become infected by feeding if recombinant viruses are occluded into PEBs by coinfection with wild type virus. Thus, the system is easily adaptable to crop spraying for infection of insect pest populations. Alternatively, the antisense inserts can be positioned downstream of another strong viral promoter, such as P10, to produce recombinant progeny with the intact polyhedrin gene, thus producing recombinant PIBs.

It should be understood that the foregoing relates only to preferred embodiments of the present invention and that many modifications or alterations may be made therein without departing from the spirit and the scope of the invention as set forth in the claims herein.

We claim:

1. An insect control agent comprising a selectable, polyhedrin promoter-based baculovirus vector which comprises the DNA sequence of SEQ ID NO: 1 inserted downstream of the polyhedrin promoter wherein the DNA sequence is oriented such that upon transcription, an antisense RNA transcript, relative to the sense direction of c-myc, is produced.

2. An insect control agent comprising a selectable, polyhedrin promoter-based baculovirus vector which further comprises the DNA sequence of SEQ ID NO:2 inserted downstream of the polyhedrin promoter wherein the DNA sequence is oriented such that upon transcription, an antisense RNA transcript, relative to the sense direction of c-myc, is produced.

3. A method of controlling insects comprising infecting said insects with an insect control agent such that the insects are controlled, wherein said insect control agent comprises a selectable, polyhedrin promoter-based baculovirus vector comprising the sequence of SEQ ID NO: 1 inserted downstream of the polyhedrin promoter, wherein the DNA sequence is oriented such that upon transcription, an antisense RNA transcript, relative to the sense direction of c-myc, is produced and wherein the insects are of any insect species susceptible to said vector.

4. A method of controlling insects comprising infecting said insects with an insect control agent such that the insects are controlled, wherein said insect control agent comprises a selectable, polyhedrin promoter-based baculovirus vector comprising the sequence of SEQ ID NO: 2 inserted downstream of the polyhedrin promoter, wherein the DNA sequence is oriented such that upon transcription, an antisense RNA transcript, relative to the sense direction of c-myc, is produced and wherein the insects are of any insect species susceptible to said vector.

5. An insect control agent comprising a vector, which comprises a DNA sequence as set forth in SEQ ID NO: 1, and a promoter which directs transcription of the DNA sequence, wherein the DNA sequence is oriented such that upon transcription, an antisense RNA transcript, relative to the sense direction of c-myc, is produced and wherein the vector is any one to which the insect being controlled is susceptible.

6. An insect control agent comprising a vector, which comprises a DNA sequence as set forth in SEQ ID NO: 2, and a promoter which directs transcription of the DNA sequence, wherein the DNA sequence is oriented such that upon transcription, an antisense RNA transcript, relative to the sense direction of c-myc, is produced and wherein the vector is any one to which the insect being controlled is susceptible.

7. A method of controlling insects comprising the step of infecting said insects with a vector, which comprises a DNA sequence as set forth in SEQ ID NO: 1, and a promoter which directs transcription of the DNA sequence, wherein the DNA sequence is oriented such that upon transcription, an antisense RNA transcript, relative to the sense direction of c-myc, is produced and wherein the vector is any one to which the insect being controlled is susceptible.

8. A method of controlling insects comprising the step of infecting said insects with a vector, which comprises a DNA sequence as set forth in SEQ ID NO: 2, and a promoter which directs transcription of the DNA sequence, wherein the DNA sequence is oriented such that upon transcription, an antisense RNA transcript, relative to the 'sense direction of c-myc, is produced and wherein the vector is any one to which the insect being controlled is susceptible.

9. The insect control agent of claim 5, wherein the promoter is a viral promoter.

10. The insect control agent of claim 9, wherein the promoter is selected from the group consisting of the polyhedrin promoter and the P10 promoter.

11. The insect control agent of any one of claims 5, 9 and 10, wherein the vector is a baculovirus.

12. The insect control agent of claim 11, wherein the baculovirus is a granulosis virus.

13. The insect control agent of claim 6, wherein the promoter is a viral promoter.

14. The insect control agent of claim 13, wherein the promoter is selected from the group consisting of the polyhedrin promoter and the P10 promoter, 15. The insect control agent of any one of claims 6, 13 and 14, wherein the vector is a baculovirus.

16. The insect control agent of claim 15, wherein the baculovirus is a granulosis virus.

17. The method of controlling insects of claim 7, wherein the promoter is a viral promoter.

18. The method of controlling insects of claim 17, wherein the promoter is selected from the group consisting of the polyhedrin promoter and the P10 promoter.

19. The method of controlling insects of any one of claims 7, 17 and 18, wherein the vector is a baculovirus.

20. The method of controlling insects of claim 19, wherein the baculovirus is a granulosis virus.

21. The method of controlling insects of claim 8, wherein the promoter is a viral promoter.

22. The method of controlling insects of claim 21, wherein the promoter is selected from the group consisting of the polyhedrin promoter and the P10 promoter.

23. The method of controlling insects of any one of claims 8, 21 and 22, wherein the vector is a baculovirus.

24. The method of controlling insects of claim 23, wherein the baculovirus is a granulosis virus.

* * * * *

SEQUENCE LISTING

```
(1) GENERAL INFORMATION:

(iii) NUMBER OF SEQUENCES: 2

(2) INFORMATION FOR SEQ ID NO: 1:

(i) SEQUENCE CHARACTERISTICS:
          (A) LENGTH: 370 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 1:

CCAGTGAGGA CATTTGGAAG AAGGTATAAT TTAGGTGCGT TAAGTAGCAG AAACATCAAT     60

TCCTTATTTT AATTTCCAAG AAAATGGTAA TTATACAGGT GATTCGGGAG TGAGCAGGAC    120

CAACCAGCAG TATTTAGTAA GTTCTTTTTG TTTTAATGTT CGCATACAGA ATTAAAGTAC    180

CATAATTAAA GTGTGGGTGG GGTTTACTAA ATATGATTGT GAAGGACCCA TTATGAATTA    240

CTGAGGGTGT AATTGTTCCT GCTTACGTCT CCTGAATTAC ACTATAGTAC CGACGTTAGG    300

CATTTCAGGA AAACTCACTG TTTTCCTGCA GTTTGTACAA GAAGAAATCC CTCTGCTGTA    360

TGCCCATACC                                                           370

(2) INFORMATION FOR SEQ ID NO: 2:

(i) SEQUENCE CHARACTERISTICS:
          (A) LENGTH: 757 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iii) ANTI-SENSE: NO
```

-continued (xi) SEQUENCE DESCRIPTION: SEQ ID NO: 2:

```
CGCCCAGCGA GGATATCTGG AAGAAATTCG AGCTGCTGCC CACCCCGCCC CTGTCCCCTA      60

GCCGCCGCTC CGGGCTCTGC TCGCCCTCCT ACGTTGCGGT CACACCCTTC TCCCTTCGGG     120

GAGACAACGA CGGCGGTGGC GGGAGCTTCT CCACGGCCGA CCAGCTGGAG ATGGTGACCG     180

AGCTGCTGGG AGGAGACATG GTGAACCAGA GTTTCATCTG CGACCCGGAC GACGAGACCT     240

TCATCAAAAA CATCATCATC CAGGACTGTA TGTGGAGCGG CTTCTCGGCC GCCGCCAAGC     300

TCGTCTCAGA GAAGCTGGCC TCCTACCAGG CTGCGCGCAA AGACAGCGGC CCTGCAGGAT     360

CTGAGCGCCG CCGCCTCAGA GTGCATCGAC CCCTCGGTGG AGCCCGAACC CCGCCCGCGG     420

CCACAGCGTC TGCTCCACCT CCAGCTTGTA TCTTCCCCTA CCCTCTCAAC GACAGCAGCT     480

CGCCCAAGTC CTGCGCCTCG CAAGACTCCA GCGCCTTCTC TCCGTCCTCG GATTCTCTGC     540

TCTCCTCGAC GGAGTCCTCC CCGCAGGGCA GCCCCGAGCC CCTGGTGCTC CATGAGGAGA     600

CACCGCCCAC CACCAGCAGC GACTCTGGTA AGCGAAGCCC GCCCAGGCCT GTCAAAAGTG     660

GGCGGCTGGA TACCTTTCCC ATTTTCATTG GCAGCTTATT TAACGGGCCA CTCTTATTAG     720

GAAGGAGAGA TAGCAGATCT GGAGAGATTT GGGAGCT                             757
```